(12) United States Patent
Cox

(10) Patent No.: US 10,695,121 B2
(45) Date of Patent: Jun. 30, 2020

(54) METHOD AND SYSTEM OF CONTROLLING CONDUCTIVE FLUID FLOW DURING AN ELECTROSURGICAL PROCEDURE

(71) Applicant: ArthroCare Corporation, Austin, TX (US)

(72) Inventor: David A. Cox, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 149 days.

(21) Appl. No.: 15/715,383

(22) Filed: Sep. 26, 2017

(65) Prior Publication Data

US 2018/0014873 A1    Jan. 18, 2018

Related U.S. Application Data

(62) Division of application No. 13/800,266, filed on Mar. 13, 2013, now Pat. No. 9,801,678.

(51) Int. Cl.
*A61B 18/14* (2006.01)
*A61B 18/00* (2006.01)
*A61B 17/00* (2006.01)

(52) U.S. Cl.
CPC .......... *A61B 18/14* (2013.01); *A61B 18/1402* (2013.01); *A61B 18/1492* (2013.01); *A61B 2017/00207* (2013.01); *A61B 2018/00011* (2013.01); *A61B 2018/00029* (2013.01); *A61B 2018/00035* (2013.01); *A61B 2018/0091* (2013.01); *A61B 2018/00166* (2013.01); *A61B 2018/00642* (2013.01);
(Continued)

(58) Field of Classification Search
CPC ..... A61B 18/1492; A61B 18/02; A61B 18/14; A61B 18/1402; A61B 2018/00011; A61B 2018/0022; A61B 2018/00214; A61B 2018/00863; A61B 2018/0642; A61B 5/14; A61B 5/1402
USPC ......................................................... 606/34
See application file for complete search history.

(56) References Cited

U.S. PATENT DOCUMENTS

| 2004/0230262 A1* | 11/2004 | Sartor | A61B 18/1402 607/96 |
| 2005/0212870 A1* | 9/2005 | Chiao | A61M 35/00 347/76 |

(Continued)

FOREIGN PATENT DOCUMENTS

| GB | 2451623 | 2/2009 |
| GB | 2477353 | 8/2011 |

OTHER PUBLICATIONS

Office Action for German Patent Application No. 102014003288.4 dated Jun. 26, 2018, 12 pages.

*Primary Examiner* — Carl H Layno
*Assistant Examiner* — Pamela M. Bays
(74) *Attorney, Agent, or Firm* — Norman F. Hainer, Jr.

(57) ABSTRACT

Controlling conductive fluid flow during an electrosurgical procedure. At least some of the example embodiments are methods including: flowing conductive fluid from a source lumen to a suction lumen of an electrosurgical wand, the flowing with the electrosurgical wand in a first orientation; sensing a change in orientation of the electrosurgical wand to a second orientation different than the first orientation; and changing a control parameter associated with the conductive fluid flow, the changing responsive to the change in orientation of the electrosurgical wand.

18 Claims, 10 Drawing Sheets

(52) U.S. Cl.
CPC ............... *A61B 2018/00744* (2013.01); *A61B 2018/00916* (2013.01); *A61B 2018/1472* (2013.01); *A61B 2218/002* (2013.01); *A61B 2218/007* (2013.01)

(56) References Cited

U.S. PATENT DOCUMENTS

| | | | |
|---|---|---|---|
| 2008/0097476 A1* | 4/2008 | Peh | A61B 1/0008 606/130 |
| 2009/0048592 A1 | 2/2009 | Thomas | |
| 2012/0191089 A1* | 7/2012 | Gonzalez | A61B 18/1485 606/45 |

* cited by examiner

METHOD AND SYSTEM OF CONTROLLING CONDUCTIVE FLUID FLOW DURING AN ELECTROSURGICAL PROCEDURE

CROSS-REFERENCE TO RELATED APPLICATIONS

This application is a divisional of U.S. patent application Ser. No. 13/800,266 filed Mar. 13, 2013, now issued as U.S. Pat. No. 9,801,678 the complete disclosure of which are incorporated herein by reference for all purposes.

BACKGROUND

Electrosurgical procedures can be classified, at some level, based on the location associated with the body at which the procedure takes place. "Wet field" procedures generally take place inside the body, such as within the shoulder or within the knee. "Dry field" procedures generally take place on an outer surface of the body or surfaces exposed to atmosphere, such as the skin, within the mouth, or within the nasopharynx.

Regardless of whether a procedure is a wet field or dry field procedure, in most cases saline is delivered to the treatment site; however, in dry field procedures excess saline can easily migrate and cause secondary issues. For example, excess saline accumulating in the throat during procedures in the nose or mouth can cause unintended flow paths for electrical current through the body, or may allow the saline to enter the lungs.

Any advance that better controls saline fluid in and around the electrodes of an electrosurgical system would provide a competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
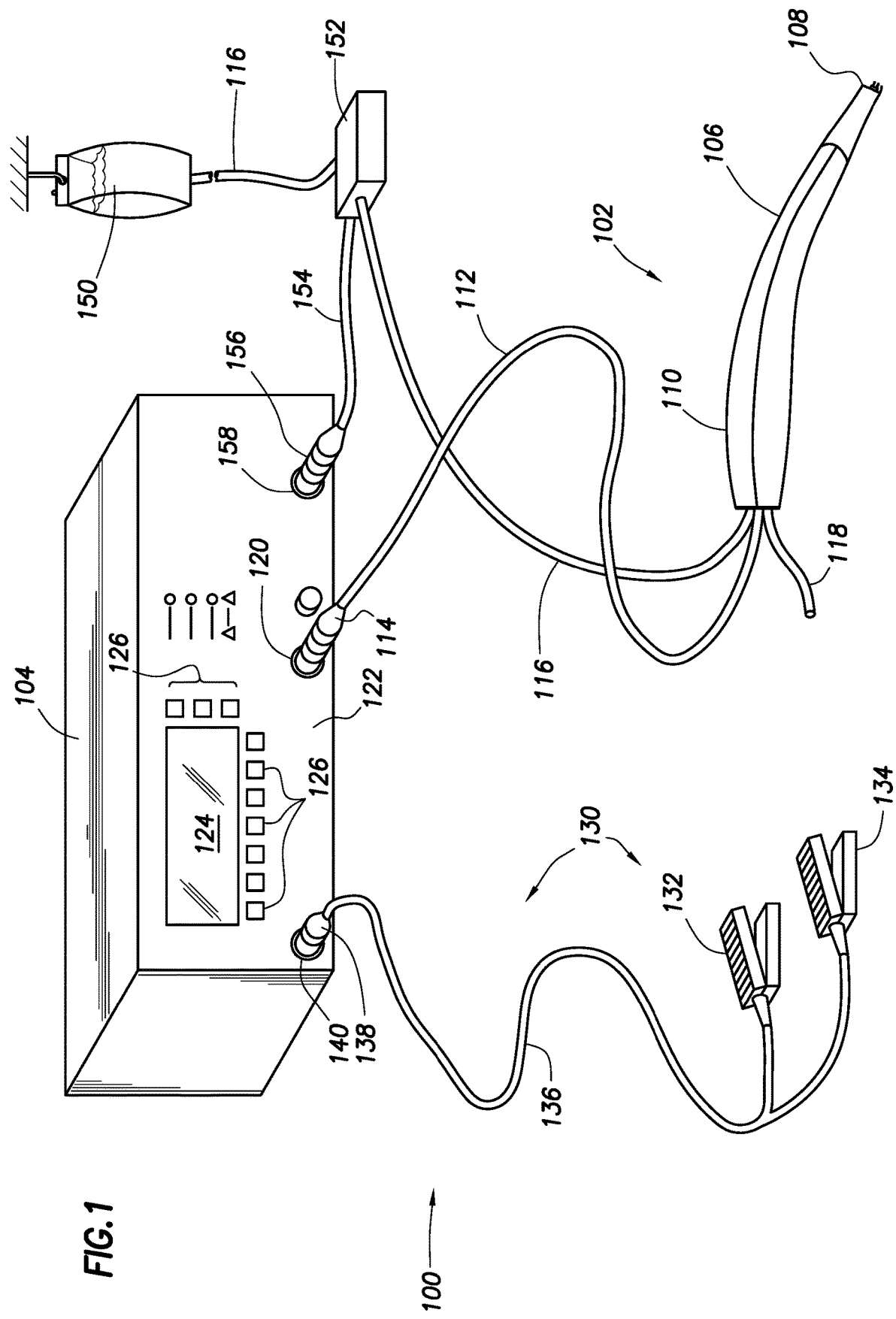
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow return path with respect to an active electrode, and/or an electrode of an electrical surgical wand which does not itself produce an electrically-induced tissue-altering effect on tissue targeted for treatment.

A fluid conduit said to be "within" an elongate housing shall include not only a separate fluid conduit that physically resides within an internal volume of the elongate housing, but also situations where the internal volume of the elongate housing is itself the fluid conduit.

"Orientation", with regard to an electrosurgical wand, shall mean inclination of the distal end of wand relative to the handle end of the wand, elevation of the distal end of the wand (e.g., relative to a source of conductive fluid), rotational orientation of the wand, or a combination thereof.

"Three-axis gyroscope" shall refer to a sensor that senses positional changes in position in all three spatial directions.

"Six-axis gyroscope" shall refer to a sensor that senses positional changes in position in all three spatial directions, and also senses acceleration in all three spatial directions.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application.

Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate housing 106 that defines distal end 108 where at least some electrodes are disposed. The elongate housing 106 further defines a handle or proximal end 110. The wand 102 further comprises a flexible multi-conductor cable 112 housing a plurality of electrical and/or communicative conductors (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a first flexible tubular member 116 and a second flexible tubular member 118. In some embodiments, the flexible tubular member 116 is used to provide a conductive fluid (e.g., saline) to the distal end 108 of the wand. In an example system, the flexible tubular member 116 is a hose or tubing having a 0.152 inch outside diameter, and a 0.108 inch inside diameter, but other sizes may be equivalently used. In the example system of FIG. 1, the source of the conductive fluid is a saline bag 150, with the saline flowing through an intermediate flow control device 152 prior to reaching the wand 102. The flow control strategy implemented by the flow control device 152 is discussed in greater detail below. The flow control device 152 comprises a flexible multi-conductor cable 154 housing a plurality of electrical and/or communicative conductors (not specifically shown in FIG. 1), and the flexible multi-conductor cable 154 terminates in a connector 156. As shown in FIG. 1, the flow control device couples to the controller 104, such as by a controller connector 158 on an outer surface 122 (in the illustrative case of FIG. 1, the front surface). Thus, in the example system the electrosurgical controller 104 communicatively couples to and controls operation of the flow control device 152.

In some embodiments, flexible tubular member 118 is used to provide suction for aspiration at the distal end 108 of the wand. The suction for aspiration may be provided from any suitable source (e.g., wall suction in a hospital environment, or suction provided from a peristaltic pump). In one example system, the flexible tubular member 118 is a hose having a 0.25 inch outside diameter, and a 0.17 inch internal diameter, but other sizes may be equivalently used.

Still referring to FIG. 1, the controller 104 controllably provides energy to the wand 102 for the electrosurgical procedures (discussed more below). A display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. The foot pedal assembly 130 may be used to control various aspects of the controller 104, such as the operational mode. For example, a pedal device, such as pedal device 132, may be used for on-off control of the application of radio frequency (RF) energy to the wand 102. A second pedal device, such as pedal device 134, may be used to control and/or set the operational mode of the electrosurgical system. For example, actuation of pedal device 134 may switch between energy levels. In yet still further embodiments, the wand 102 may further comprise switches accessible on an outside portion, where the switches may control the operational modes of the controller 104.

The electrosurgical system 100 of the various embodiments may have a variety of operational modes. One such mode employs Coblation® technology. In particular, the assignee of the present disclosure is the owner of Coblation® technology. Coblation® technology involves the application of a RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region near the one or more active electrodes and the target tissue. Electrically conductive fluid may be inherently present in the body, such as blood, puss, or in some cases extracellular or intracellular fluid. In other embodiments, the electrically conductive fluid may be a liquid or gas, such as isotonic saline. In a particular embodiment of wound treatment, the electrically conductive fluid is delivered in the vicinity of the active electrode and/or to the target site by the wand 102, such as by way of the internal fluid conduit and flexible tubular member 116.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation® mode, the electrosurgical system 100 of FIG. 1 may also in particular situations be useful for sealing blood vessels, when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue.

A more complete description of the various phenomena can be found in commonly assigned U.S. Pat. Nos. 6,355, 032; 6,149,120 and 6,296,136, the complete disclosures of which are incorporated herein by reference.

Figure 2:
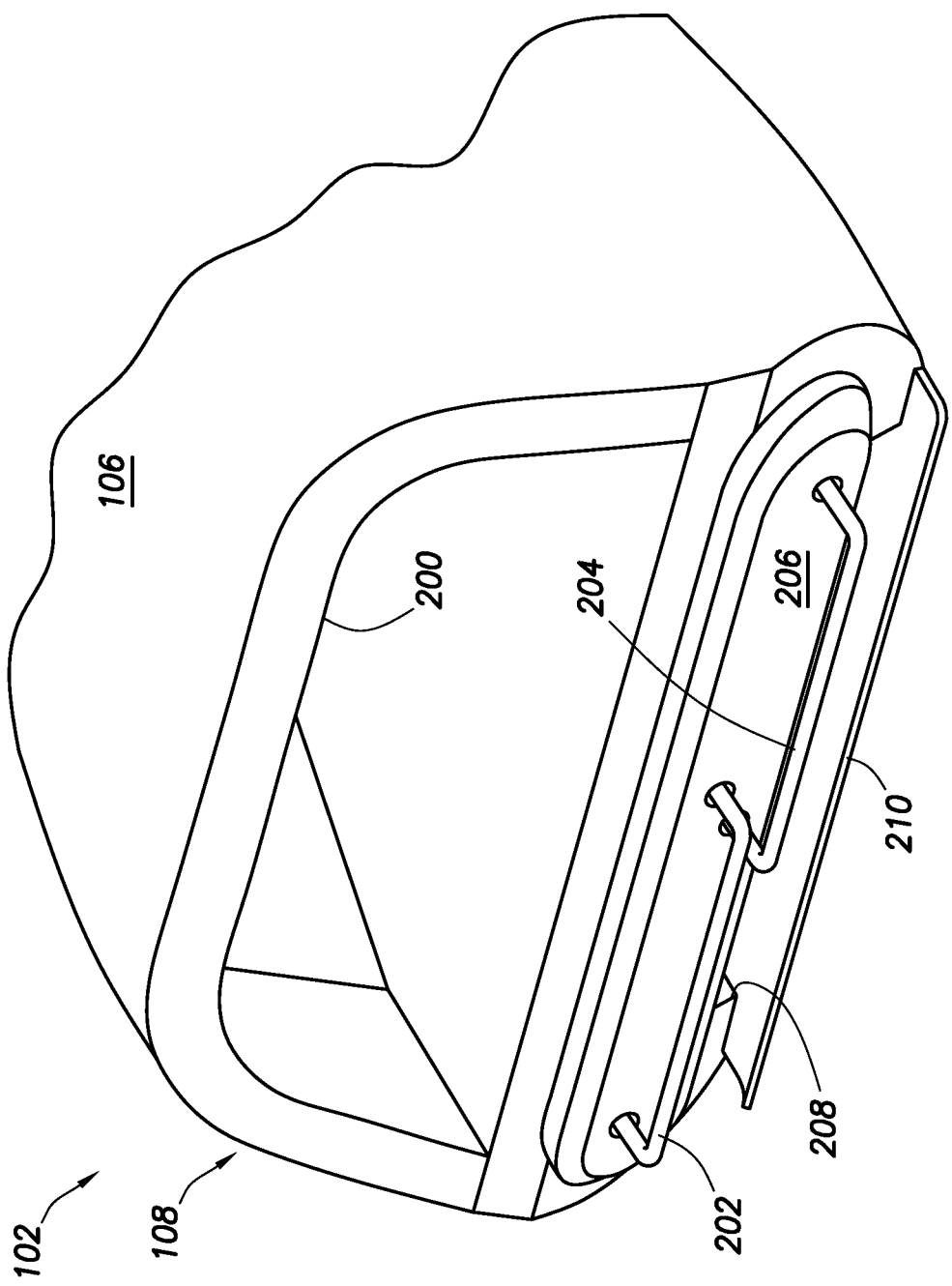
FIG. 2 shows a perspective view a portion of a wand in accordance with at least some embodiments.

FIG. 2 illustrates a perspective view of the distal end 108 of wand 102 in accordance with an example system. In particular, in the example system the wand 102 is a wound care wand enabled for use to treat wounds on a patient's skin. Other types of wands may be used in the example system. For example, the PROCISE® Max Plasma Wand available from AthroCare Corporation of Austin, Tex., is designed and constructed for use in the mouth and throat may be used, such as for tonsillectomies. As a further example, wands designed in constructed for use in the nasopharynx may be used, such as for removal of portions of the soft palate and/or removal of polyps for treatment of sleep apnea. The relative proportions of the components of wands designed for different treatments will differ, but regardless of size and proportion wands for dry field use will comprise the same base components: an active electrode; a return electrode; a source or discharge lumen from which conductive fluid flows; and a suction or aspiration lumen in which conductive fluid and ablated tissue is aspirated away from the treatment site.

The illustrative wand 102 of FIG. 2 has a suction lumen 200, two active electrodes 202 and 204, a support member 206, a source lumen 208, and a return electrode 210. The support member 206 is coupled to the elongate housing 106. In a particular embodiment, the elongate housing 106 and handle 110 (FIG. 1) are made of a non-conductive plastic material, such as polycarbonate. In yet other embodiments, the handle 110 and/or elongate housing 106 may be constructed in whole or in part of metallic material, but the metallic material may be non-grounded and/or not provide a return path for electrons to the controller 104. Further, support member 206 is a non-conductive material resistant to degradation when exposed to plasma. In some cases support member 206 is made of a ceramic material (e.g., alumina ceramic), but other non-conductive materials may be equivalently used (e.g., glass).

An illustrative two active electrodes 202 and 204 are coupled to the support member 206. Each active electrode is a metallic structure, around which plasma is created during use in some operational modes. In some case, the wire is stainless steel, but other types of metallic wire (e.g., tungsten, molybdenum) may be equivalently used. As illustrated, each active electrode 202 and 204 is a loop of wire having a particular diameter. In wands designed for other uses (e.g., ablation of tissue of the soft palate), the active electrode may take the form of a screen or metallic plate with one or more apertures through the metallic plate leading to the suction lumen. Each example active electrode 202 and 204 is electrically coupled to the controller 104 (FIG. 1). In some cases, the active electrodes 202 and 204 are coupled to the controller by way of respective standoff portions and an insulated conductor (not specifically shown) that runs through the elongate housing 106. Thus, by way of the cable 112 (FIG. 1) and electrical pins (shown and discussed below) in the connector 114 (FIG. 1), the active electrodes 202 and 204 couple to the controller 104 (FIG. 1).

FIG. 2 further shows a source lumen 208. The source lumen 208 as illustrated is rectangular, where the long dimension is aligned with the width W. Rectangular shaped source lumen are merely illustrative, and any suitable shape may be equivalently used (e.g., circular, oval, square). The source lumen 208 is fluidly coupled within the elongate housing 106 to flexible tubular member 116 (FIG. 1), through which conductive fluids flow during use. Thus, during use, conductive fluid flows into the flexible tubular member 116 (FIG. 1), through one or more fluid conduits (not specifically shown) within the elongate housing 106, and out of the source lumen 208.

The distal end 108 of the example wand 102 further comprises a return electrode in the form of a conductive plate 210. In particular, the conductive plate 210 abuts the source lumen 208, and in the embodiments of FIG. 2 a portion of the conductive plate 210 at least partially defines the outer aperture of the source lumen 208. The conductive plate 210 is made of conductive material, which conductive material forms a return path for electrical current associated with energy applied to the active electrodes. In some cases the conductive plate 210 is made of stainless steel, but other types of metals (e.g., tungsten, molybdenum) may be equivalently used. The illustrative conductive plate 210 is oriented such that at least some of the saline flowing through the fluid conduit 218 contacts the conductive plate 210 before contacting an adjacent wound or contacting the active electrodes 202 and 204. Conductive plate 210 is electrically coupled to the controller 104 (FIG. 1). In some cases, the conductive plate 210 is coupled to the controller by way of an insulated conductor (not specifically shown) that runs through the elongate housing 106. Thus, by way of the cable 112 (FIG. 1) and electrical pins in the connector 114 (FIG. 1), the conductive plate 210 couples to the controller 104 (FIG. 1).

FIG. 2 also illustrates that a wand 102 in accordance with at least some embodiments further comprises a suction lumen 200. The suction lumen 200 is fluidly coupled to the flexible tubular member 118 (FIG. 1) by way of fluid conduit (not specifically shown) within the wand 102. Thus, and as the name implies, the suction lumen 204 is used to remove byproducts of wound treatment using the wand 102, such as removal of conductive fluid, molecularly disassociated tissue, and tissue separated from the wound but otherwise still intact. In example operation of a wand for wound care, aggressive aspiration is contemplated to enable removal of larger pieces of tissue not molecularly disassociated. In some cases, the aspiration may be created by an applied pressure between and including 100 millimeters of mercury (mmHg) and 400 mmHg below atmospheric.

Some example wands for dry field procedures are designed and constructed such that the conductive fluid flow exits the source lumen, flows to and/or across the active electrode(s), and then is aspirated into the suction lumen. In the example case of FIG. 2, the conductive plate 210 has a lip portion on the distal end of plate that directs conductive fluid discharged from the source lumen 208 toward the active electrodes. A plasma may be created proximate the active electrodes during periods of time when RF energy is applied to the active electrodes, and then the conductive fluid and ablation byproducts are aspirated into the suction lumen 204. The specification now turns to shortcomings of related-art devices.

The inventors of the present specification have found a shortcoming of related-art devices in the form of variable conductive fluid flow based on orientation of the wand. In the related-art, prior to performing the surgical procedure the conductive fluid flow is manually adjusted, such as by partially clamping the tubing member 116 (e.g., clamping using a hemostat). The adjustment involves setting a flow of conductive fluid out of the source lumen that is substantially aspirated back into the suction lumen (i.e., no or very few drips of conductive fluid when the fluid is flowing out the source lumen). Once the flow of conductive fluid is set, the surgeon performs the procedure; however, an issue arises related to the orientation of the wand, which issue is illustrated with respect to FIGS. 3-5.

Figure 3:
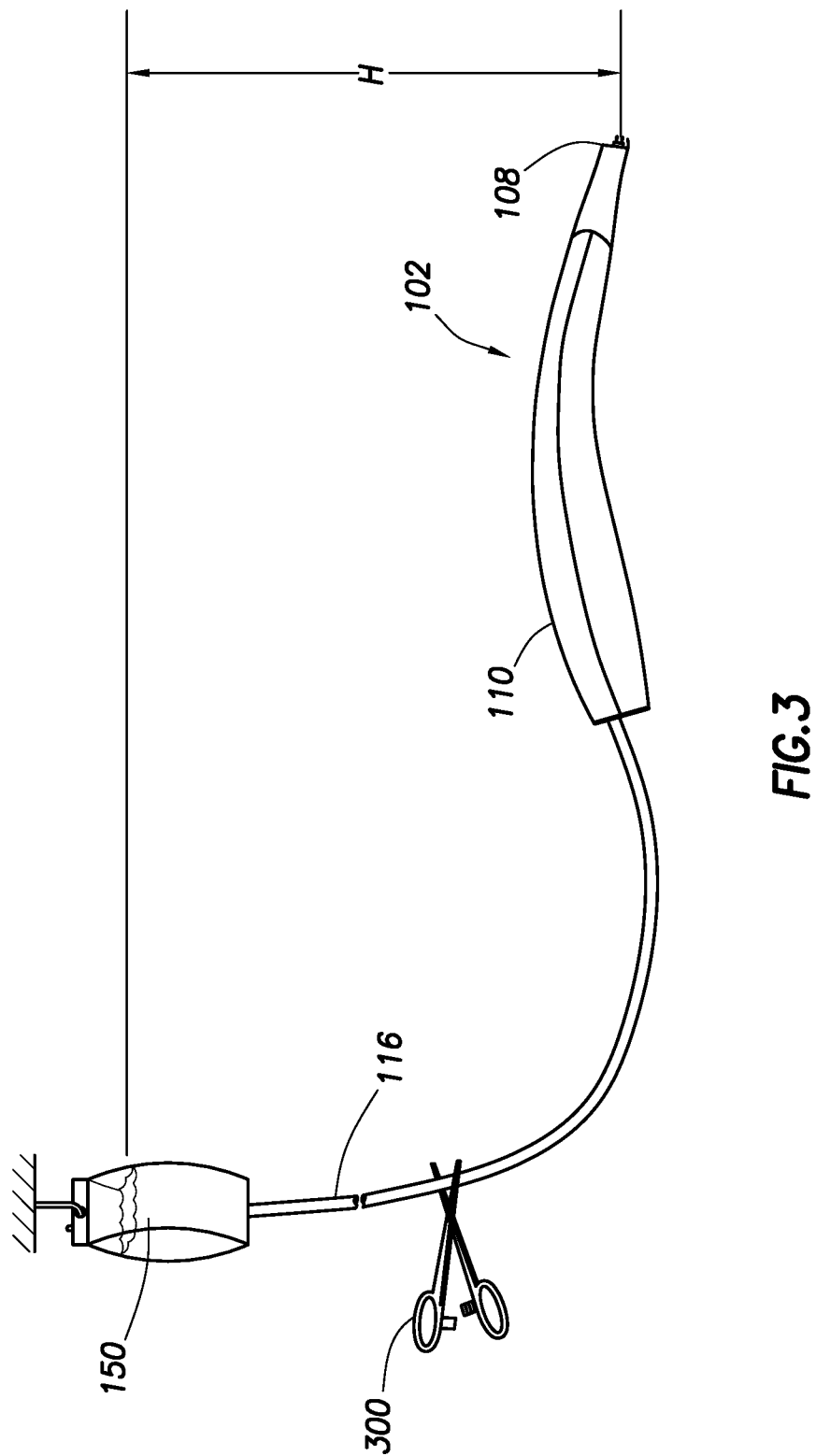
FIG. 3 shows an elevation view of a system in order to describe shortcomings of the related-art.

FIG. 3 shows an elevation view of a wand 102 with the tubing member 116 coupled to a source of conductive fluid in the form of a saline bag 150. The remaining tubing and cables are not shown so as not to unduly complicate the figure. Consider, for purposes of explanation, that prior to the surgical procedure the wand 102 is held in the orientation shown in FIG. 3, where the handle end 110 and the distal end 108 are at substantially the same elevation. Held in the orientation shown in FIG. 3, a surgeon may adjust the flow of the conductive fluid (e.g., by adjusting the clamping force of hemostat 300) such that there are no or very few drips of conductive fluid from the distal end of the wand 102 (i.e., most if not all the conductive fluid flow is aspirated into the suction lumen). In the orientation shown in FIG. 3, a certain amount of pressure of conductive fluid exists related to the relative elevation between the distal end 108 of the wand and the fluid level in the saline bag 150, as shown by relative height H.

Figure 4:
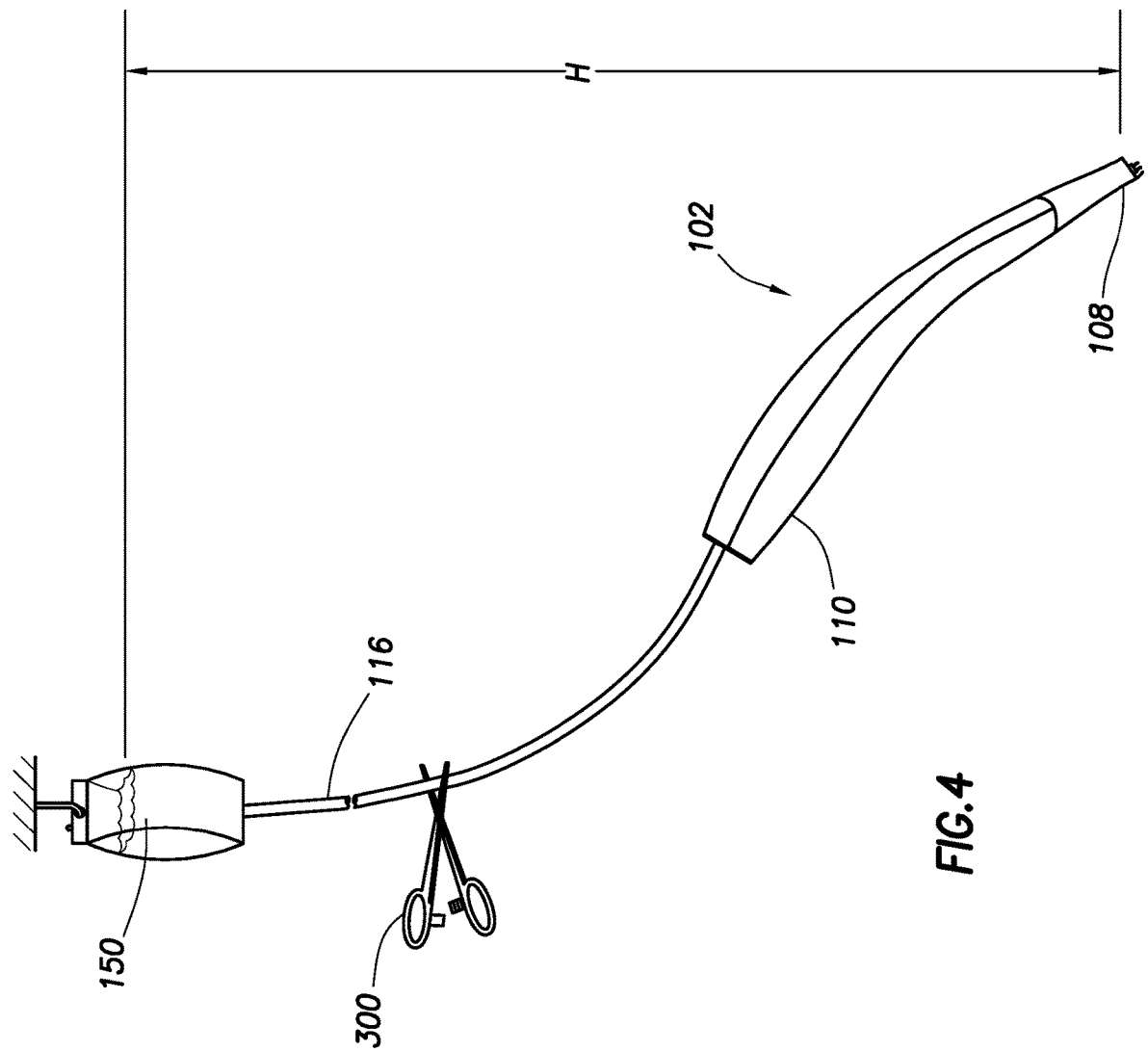
FIG. 4 shows an elevation view of a system in order to describe shortcomings of the related-art.

Now consider that during use the surgeon changes the inclination of the distal end 108 in relation to the handle end 110. Stated another way, consider that the elevation of the distal end 108 changes such that the relative height H changes. FIG. 4 shows an elevation view of wand 102 with the tubing member 116 coupled to a source of conductive fluid in the form of a saline bag 150, but where the orientation of the distal end 108 has changed in relation to the handle end 110. In particular, in FIG. 4 the inclination of the wand 102 has changed such that the distal end 108 is lower than the handle end 110 (with the handle end held at a constant elevation), and in so doing the relative height H has increased (considered against the FIG. 3). Given the static restriction to flow illustrated by the hemostat 300, the change in relative height H results in greater conductive fluid flow out of the source lumen at the distal end 108 of wand. The greater conductive fluid flow may result in unintended pooling of conductive fluid, which may have several adverse consequences, such as unintended current paths for the flow of electrical current, and conductive fluid accumulating in undesirable locations like the lungs.

Figure 5:
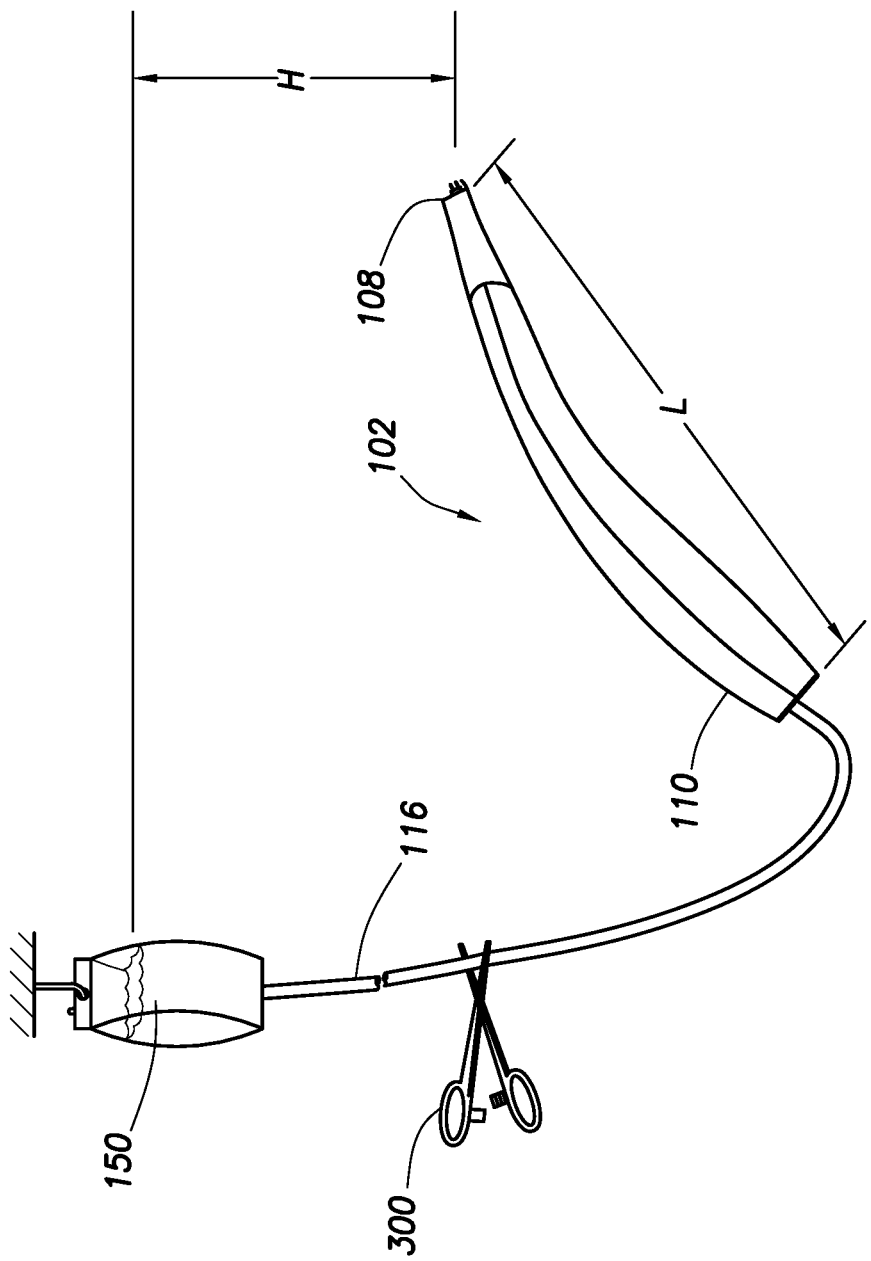
FIG. 5 shows an elevation view of a system in order to describe shortcomings of the related-art.

Now consider that during use, the surgeon changes the orientation of the distal end 108 in relation to the handle end 110 as shown in FIG. 5. FIG. 5 shows an elevation view of wand 102 with the tubing member 116 coupled to a source of conductive fluid in the form of a saline bag 150, but where inclination of the wand 102 has changed such that the distal end 108 is higher than the handle end 110, and in so doing the relative height H has decreased. Again, given the static restriction to flow illustrated by the hemostat 300, the change in relative height H (as compared to either FIG. 3 or FIG. 4) results in less conductive fluid flow out of the source lumen at the distal end 108 of wand. Less conductive fluid flow may also result in inadequate wetting of the active electrodes, and thus inefficient ablation or arterial sealing.

In some example systems, the length L of the wand 102 measured from the handle end 110 to the distal end 108 may be six to eight inches. It follows that, even holding the handle end 110 at a constant elevation, the change in elevation of the distal end 108 caused by the change in inclination as between FIGS. 4 and 5 could be significant, on the order of 12-16 inches. Moreover, in use the surgeon may not hold the handle end 110 at a constant elevation relative to the fluid level in the saline bag 150, resulting in further changes in relative height H, each of which results in a change in conductive fluid flow.

In accordance with the various embodiments, the issues associated with changes in conductive fluid flow based on changes in relative height H are addressed, at least in part, by a system and related method which senses changes in orientation of the wand 102, and automatically (i.e., without human involvement at the time of the change) compensates for orientation changes of the wand 102 and/or changes in elevation of the wand 102 (even if orientation remains constant).

Figure 6:
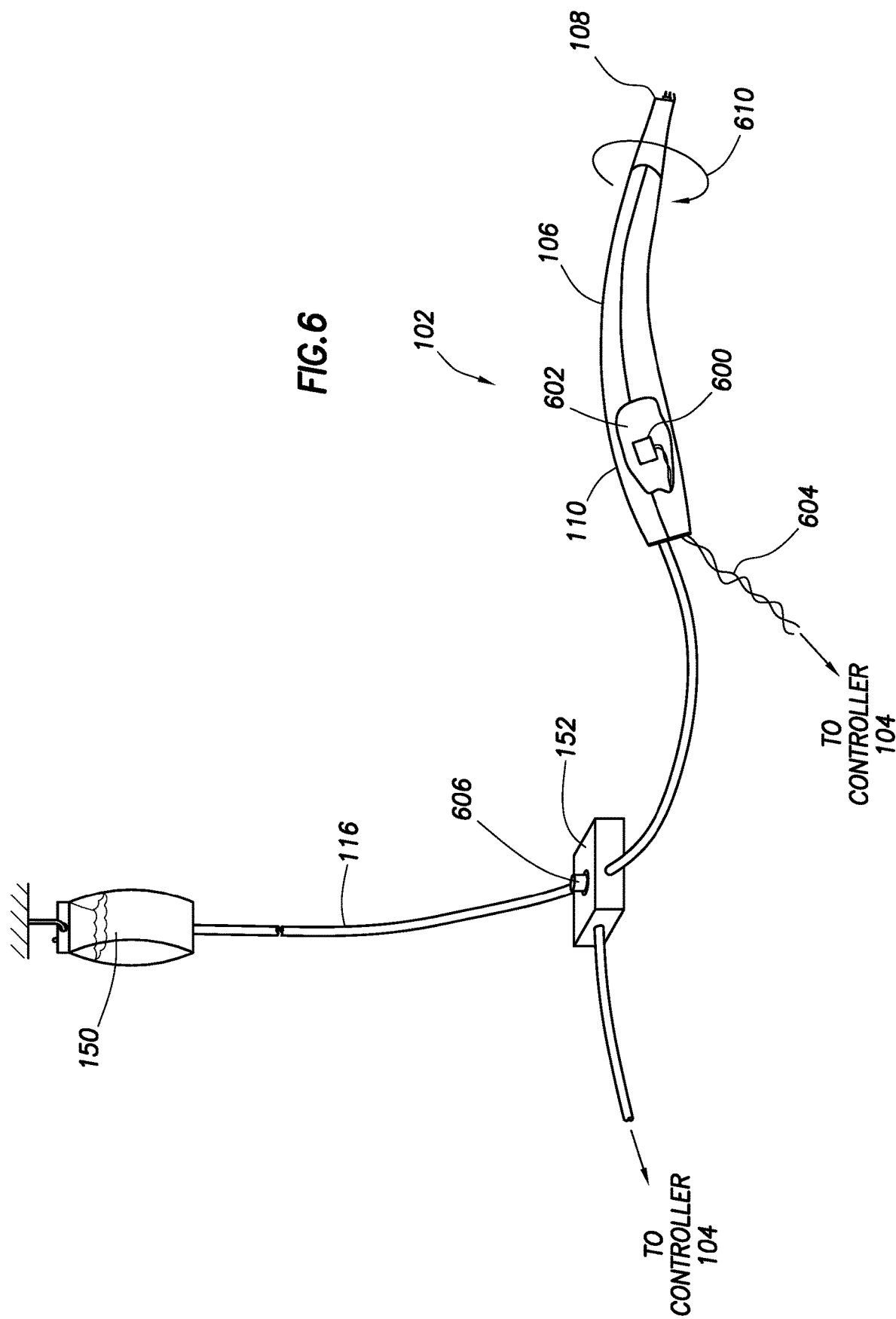
FIG. 6 shows an elevation view of a (partial) system in accordance with at least some embodiments.

FIG. 6 shows an elevation view of wand 102 with the tubing member 116 coupled to a source of conductive fluid in the form of a saline bag 150, but also additional devices to implement in the various example embodiments. In particular, FIG. 6 shows, in partial cutaway, that wand 102 in accordance with example systems comprises an orientation sensor 600. Orientation sensor 600 mechanically couples to the wand (and as shown mechanically couples within an interior volume 602 defined by the wand). Moreover, the orientation sensor 600 communicatively couples to the controller 104, such as by way of conductors 604 (which conductors may reside within the multi-conductor cable 112 of FIG. 1). As the name implies, the orientation sensor 600 senses orientation of the wand 102. The orientation sensor 600 may take many suitable forms, examples of which are discussed more thoroughly below. The example system of FIG. 6 further comprises flow control device 152 which, in the example system, is likewise coupled to the controller 104. In accordance with various embodiments, the flow control device 152 is coupled to the tubing member 116 between the source of conductive fluid (in this example saline bag 150) and the wand 102. The flow control device is designed and constructed to present different restrictions to the flow of conductive fluid based on the orientation of the wand as sensed by the orientation sensor 600.

In accordance with the various embodiments, the surgeon holds the wand in a particular orientation, and sets the flow rate of the conductive fluid such that there are no or very few drips of conductive fluid from the distal end 108 of the wand 102 (i.e., most if not all the conductive fluid flow is aspirated into the suction lumen). Setting the flow may take many forms. In some example systems, the flow may be set or adjusted by the surgeon interfacing with controller 104, such as by pushing buttons 126. In these example systems, interaction with the controller 104 sends a signal to the flow control device to raise or lower the flow allowed to pass through the flow control device. In other cases, the flow may be set by the surgeon interfacing with an interface device 606 on the flow control device 152 itself. For example, the interface device 606 may be a knob that when rotated in a first direction increases the flow of conductive fluid, and when rotated in a second direction decreases the flow the conductive fluid.

Once the initial conductive fluid flow is set (and regardless of the mechanism by which the initial flow is set), the surgeon may begin to use the wand in the electrosurgical procedure, and in using the wand 102 the orientation of the distal end 108 may change. However, the orientation sensor 600 and flow control device 152 (and in some systems the controller 104) work together to control the flow of conductive fluid to reduce the effects of changes in pressure of conductive fluid caused by changes in orientation of the wand 102. For example, if the distal end 108 of the wand 102 is lowered, the relative height H increases which would tend to increase pressure and therefore increase conductive fluid flow; however, sensing the lowering of the distal end 108 of the wand 102 by way of the orientation sensor 600, the system increases flow restriction presented by the flow control device such that conductive fluid flow remains substantially constant. Oppositely, if the distal end 108 of the wand 102 is raised, the relative height H decreases which would tend to decrease pressure and therefore decrease conductive fluid flow; however, sensing the raising of the distal end 108 of the wand 102 by way of the orientation sensor 600, the system decreases flow restriction presented by the flow control device such that conductive fluid flow remains substantially constant.

In yet still other example systems, the control of flow implemented as a function of orientation of the wand may implement orientation specific flow control strategies that differ. For example, if the orientation sensor 600 provides an indication that the distal end 108 is lower than the handle end 110, the system may reduce flow of conductive fluid (as compared to the initial setting) as in the distal-end low orientation gravity may cause increased loss of conductive fluid. Oppositely, if the orientation sensor 600 provides an indication that the distal end 108 is higher than the handle end 110, the system may increase flow of conductive fluid (as compared to the initial setting) as in the distal-end high orientation the effects of gravity may decrease the likelihood of loss of conductive fluid.

Some orientation sensors may be able to sense rotational orientation of the wand 102, and implement rotational-orientation specific flow control strategies. For example, if the system senses that the wand is rotationally-oriented such that source lumen 208 is above the active electrodes and suction lumen, in such an orientation gravity assists the flow toward the suction lumen and thus the system may increase conductive fluid flow. Oppositely, if the system senses that the wand is rotationally-oriented such that source lumen 208 is below the active electrodes and suction lumen 200, in such an orientation gravity works against flow toward the suction lumen and thus the system may decrease conductive fluid flow to reduce the likelihood of loss of conductive fluid. The rotational-orientation changes may be implemented in addition to, or in place of, inclination and/or elevation based control of the conductive fluid flow.

The orientation sensor may take many forms. In some example systems the orientation sensor 600 is an inclinometer that provides and analog or digital value indicative of the relative positions of the handle end 110 and the distal end 108. For example, part number ADIS16209 Digital Inclinometer and Accelerometer available from Analog Device of Englewood, Colo., may be used as inclinometer. However, using an inclinometer as the orientation sensor 600 may not provide the ability to sense elevation changes (with constant inclination) or sense rotational orientation changes. Thus, in other example systems the orientation sensor 600 may be implemented with a digital gyroscope, such as a part number ITG-3050 Integrated Triple-Axis Digital-Output Gyroscope available from InvenSense, Inc. of Sunnyvale, Calif. Using a three-axis gyroscope the system may be able to sense not only changes in inclination of the wand 102, but also sense changes in elevation of the wand 102—that is, sense changes in all three spatial directions. Gyroscopes, whether digital or physical, are slow to "settle" and thus have limitations as to accuracy that reduce with continued measurement time, but where the time frame may span several seconds. Thus, in yet still further embodiments the orientation sensor 600 may be a six-axis gyroscope. "Six-axis" gyroscope is a term of art referring to a device that implements a three-axis gyroscope, as well as a corresponding three-axis accelerometer. By combining the readings of the gyroscope and accelerometer, more accurate measurements of orientation may be provided. Thus, in yet still other systems the orientation sensor 600 may be a six-axis gyroscope, such as a part no. MPU-6000/6050 Six-Axis MEMS Motion Tracking Device available from InvenSense, Inc.

Figure 7:
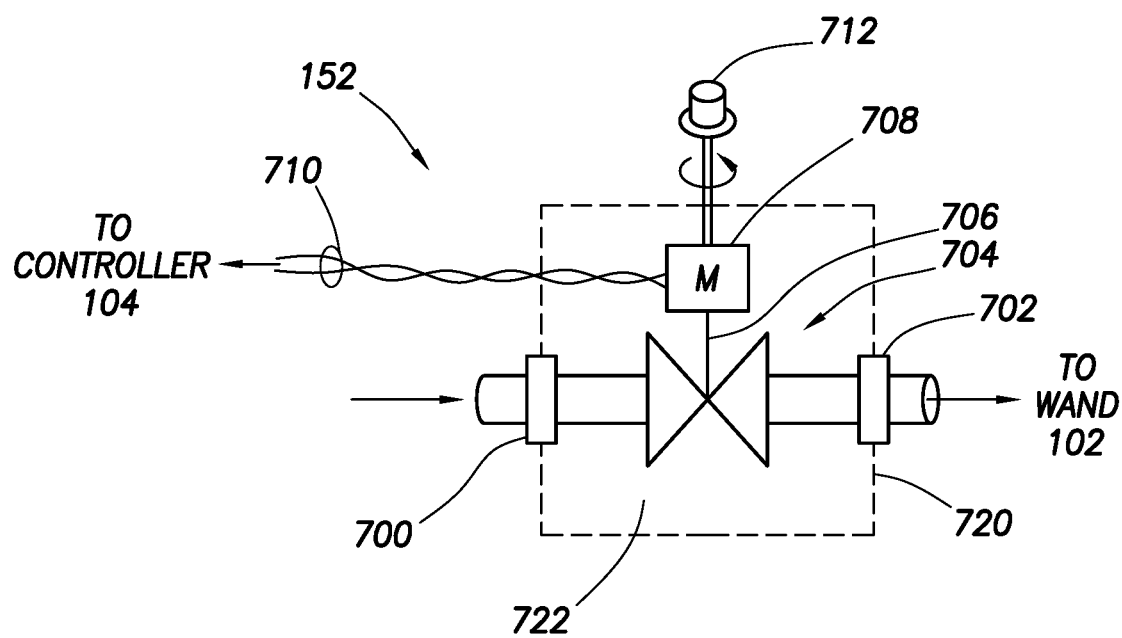
FIG. 7 shows a schematic diagram of a flow control device in accordance with at least some embodiments.

FIG. 7 shows, in schematic form, an example flow control device 152 in greater detail. In particular, the flow control device 152 comprises a first connector 700 which is designed and constructed to fluidly couple to a tubing member, such as an upstream portion of tubing member 116 coupled to a saline bag 150 (not shown in FIG. 7). Any suitable connector or connection system may be used, such as a barbed connector, or any of a variety of snap together "quick connectors". Likewise, the flow control device has a second connector 702 which is designed and constructed to fluidly couple to a tubing member, such as the downstream portion of tubing member 116 coupled to a wand 102 (not shown in FIG. 7). Between the illustrative connectors 700 and 702 resides a valve 704. Valve 704 has a stem 706, and position of the stem 706 (e.g., rotational position, elevational position) controls the restriction to conductive fluid flow presented by the valve 704. Example valve 704 further comprises an automatic valve operator 708 which enables selective positioning of the valve stem 706 based communicative signals received over the conductors 710, in example systems the conductors 710 communicatively coupled to the controller 104. Thus, by sending signals along the conductors 710, the controller 104 may control the restriction to conductive fluid flow presented by the valve 704. In the example system of FIG. 7, the stem 706 position may also be manually adjusted based on manipulation of knob 712 (e.g., when making the initial setting of the conductive fluid flow). In other cases, however, the initial setting of conductive fluid flow is controlled electronically by the controller 104 and valve operator 704. In some example systems, the flow control device 152 may define an outer cover 720 (dashed lines) which defines an internal volume 722 within which the valve 704 resides. However, in other cases the outer cover 720 may be fully or partially omitted.

Figure 8:
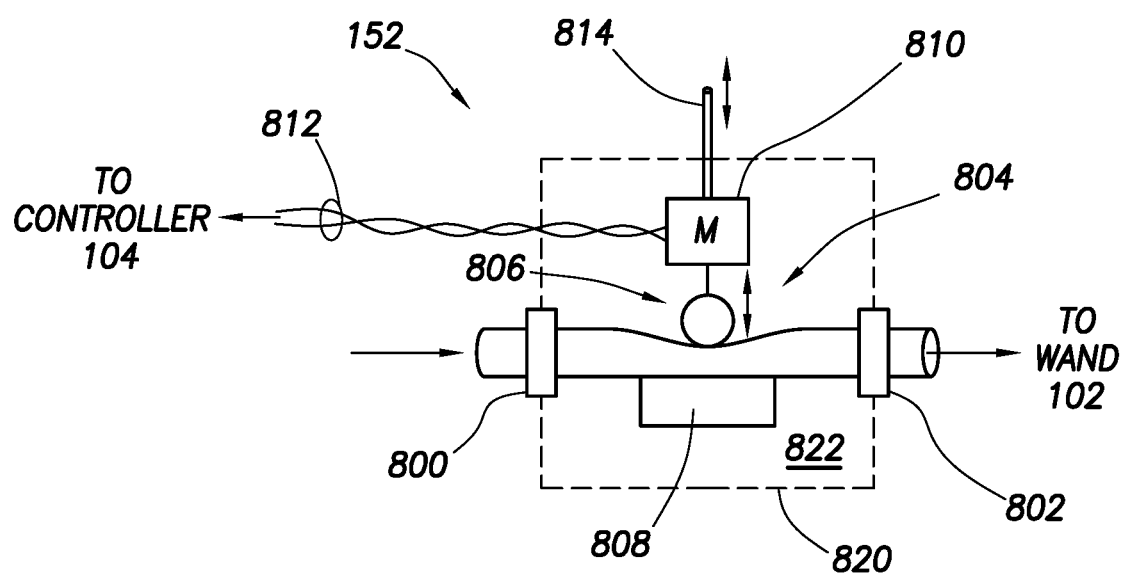
FIG. 8 shows a schematic diagram of a flow control device in accordance with at least some embodiments.

FIG. 8 shows, in schematic form, a flow control device 152 in accordance with other embodiments. In particular, the flow control device 152 comprises a first connector 800 which is designed and constructed to fluidly couple to a tubing member, such as an upstream portion of tubing member 116 coupled to a saline bag 150 (not shown in FIG. 8). Any suitable connector or connection system may be used, such as a barbed connector, or any of a variety of snap together "quick connectors". Likewise, the flow control device has a second connector 802 which is designed and constructed to fluidly couple to a tubing member, such as the downstream portion of tubing member 116 coupled to a wand 102 (not shown in FIG. 8). Between the illustrative connectors 800 and 802 resides a valve 804 in the form a pinch valve. That is, the valve 804 provides the selective control of restriction to conductive fluid flow by selectively "pinching" the tubing. Valve 804 has a stem 806, and position the stem 806 relative to the backing member 808 controls the restriction to conductive fluid flow presented by the valve 804. Example valve 804 further comprises an automatic valve operator 810 which enables selective positioning of the valve stem 806 based communicative signals received over the conductors 812, in example systems the conductors 812 communicatively coupled to the controller 104. Thus, by sending signals along the conductors 812, the controller 104 may control the restriction to conductive fluid flow presented by the valve 804. In the example system of FIG. 8, the stem 806 position may also be manually adjusted based on manipulation of feature 814 (e.g., when making the initial setting of the conductive fluid flow). In other cases, however, the initial setting of conductive fluid flow is controlled electronically by the controller 104 and valve operator 810. As before, the flow control device 152 may define an outer cover 820 (dashed lines) which defines an internal volume 822 within which the valve 804 resides. However, in other cases the outer cover 820 may be fully or partially omitted.

Figure 9:
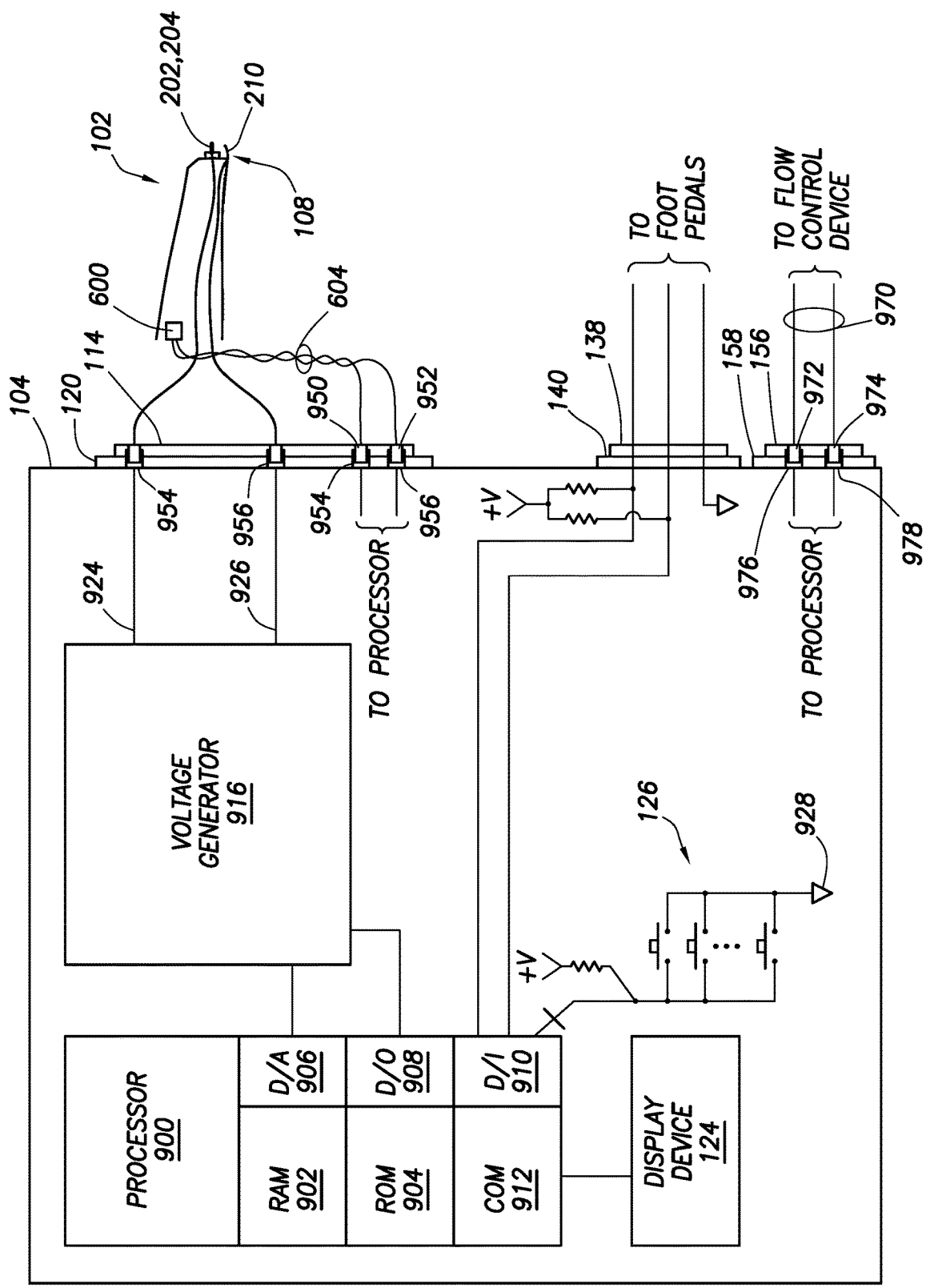
FIG. 9 shows an electrical block diagram of an electrosurgical controller in accordance with at least some embodiments.

FIG. 9 illustrates a controller 104 in accordance with at least some embodiments. In particular, FIG. 9 illustrates the controller 104 coupled to the wand 102, where the wand 102 is shown in simplified form comprising the active electrodes 202/204, the conductive plate 210 acting as a return electrode, electrical leads coupled to the controller 104, and the orientation sensor 600. The controller 104 comprises a processor 900. The processor 900 may be a microcontroller, and therefore the microcontroller may be integral with random access memory (RAM) 902, read-only memory (ROM) 904, digital-to-analog converter (D/A) 906, digital outputs (D/O) 908 and digital inputs (D/I) 910. The processor 900 may further provide one or more externally available peripheral busses, such as a serial bus (e.g., $I^2C$), parallel bus, or other bus and corresponding communication mode. The processor 900 may further be integral with a communication logic 912 to enable the processor 900 to communicate with external devices (such as the orientation sensor 600), as well as internal devices, such as display deice 124. Although in some embodiments the controller 104 may implement a microcontroller, in yet other embodiments the processor 900 may be implemented as a standalone central processing unit in combination with individual RAM, ROM, communication, D/A, D/O and D/I devices, as well as communication port hardware for communication to peripheral components.

ROM 904 stores instructions executable by the processor 900. In particular, the ROM 904 may store a software program that implements the various embodiments of controlling flow control device 152 based on orientation of the wand 102 as read from the orientation sensor 600, as well as controlling the voltage generator 816 and interfacing with the user by way of the display device 124 and/or the foot pedal assembly 130 (FIG. 1). The RAM 902 may be the working memory for the processor 900, where data may be temporarily stored and from which instructions may be executed. Processor 900 couples to other devices within the controller 104 by way of the D/A converter 906 (e.g., the voltage generator 916), digital outputs 908 (e.g., the voltage generator 916), digital inputs 910 (i.e., push button switches 126, and the foot pedal assembly 130 (FIG. 1)), and other peripheral devices.

Voltage generator 916 generates selectable alternating current (AC) voltages that are applied to the electrodes of the wand 102. In various embodiments, the voltage generator defines two terminals 924 and 926. The terminals 924 and 926 may couple to active electrodes and return electrodes. As an example, terminal 924 couples to illustrative active electrodes 202 and 204, and terminal 926 couples to the conductive plate 210 acting as return electrode. In accordance with the various embodiments, the voltage generator generates an alternating current (AC) voltage across the terminals 924 and 926. In at least some embodiments the voltage generator 916 is electrically "floated" from the balance of the supply power in the controller 104, and thus the voltage on terminals 924, 926, when measured with respect to the earth ground or common (e.g., common 928) within the controller 104, may or may not show a voltage difference even when the voltage generator 916 is active. A description of one suitable voltage generator 916 can be found in commonly assigned U.S. Pat. Nos. 6,142,992 and 6,235,020, the complete disclosure of both patents are incorporated herein by reference for all purposes.

In some embodiments, the various operational modes of the voltage generator 916 may be controlled by way of the digital-to-analog converter 906. That is, for example, the processor 900 may control the output voltage by providing a variable voltage to the voltage generator 916, where the voltage provided is proportional to the voltage generated by the voltage generator 916. In other embodiments, the processor 900 may communicate with the voltage generator by way of one or more digital output signals from the digital output 908 device, or by way of packet based communications using the communication device 912 (connection not specifically shown so as not to unduly complicate FIG. 9).

Still referring to FIG. 9, the orientation sensor 600 communicatively couples to the processor 900 by way of conductors 604 through connector 120. In an example system, male electrical pins 950 and 952 in connector 114 couple to female electrical pins 954 and 956 in connector 120, and thus by plugging connector 114 in to the connector 120, electrical connection is made. Within the controller 104 the communicative connections couple to the processor 900. There are a variety of communicative coupling scenarios possible with respect to processor 900 and orientation sensor 600, which depend in part on the type of orientation sensor used. For example, in some cases the communication from the orientation sensor may be by way of an analog signal, in which case the system would comprise electrical connection to an analog-to-digital input (not specifically shown). In other cases, the communication between the orientation sensor 600 and the processor 900 may be a digital serial communication, in which case the system would comprise electrical connection to the communication logic 912. So as not to unduly complicate the figure, the signals from the orientation sensor are shown only to couple to the processor 900. Regardless of how the processor 900 and orientation sensor 600 are communicatively coupled, by reading the orientation information from the orientation sensor 600 the processor 900, executing a program, may control the restriction to flow presented by the flow control device.

The flow control device 152 (not shown in FIG. 9) communicatively couples to the processor 900 by way of conductors 970 through connector 158. In an example system, male electrical pins 972 and 974 in connector 156 couple to female electrical pins 976 and 978 in connector 158, and thus by plugging connector 156 in to the connector 158, electrical connection is made. Within the controller 104 the communicative connections couple to the processor 900. There are a variety of communicative coupling scenarios possible with respect to processor 900 and flow control device 152, which depend in part on the type of flow control device 152. For example, in some cases the communication from the processor 900 may be by way of an analog signal, in which case the system would comprise electrical connection to the digital-to-analog module 906. In other cases, the communication between the processor 900 and the flow control device 152 may be a digital serial communication, in which case the system would comprise electrical connection to the communication logic 912. So as not to unduly complicate the figure, the signals from the flow control device are shown only to couple to the processor 900. Nevertheless, by sending signals to the flow control device the processor 900, executing a program, may control the restriction to flow presented by the flow control device.

Figure 10:
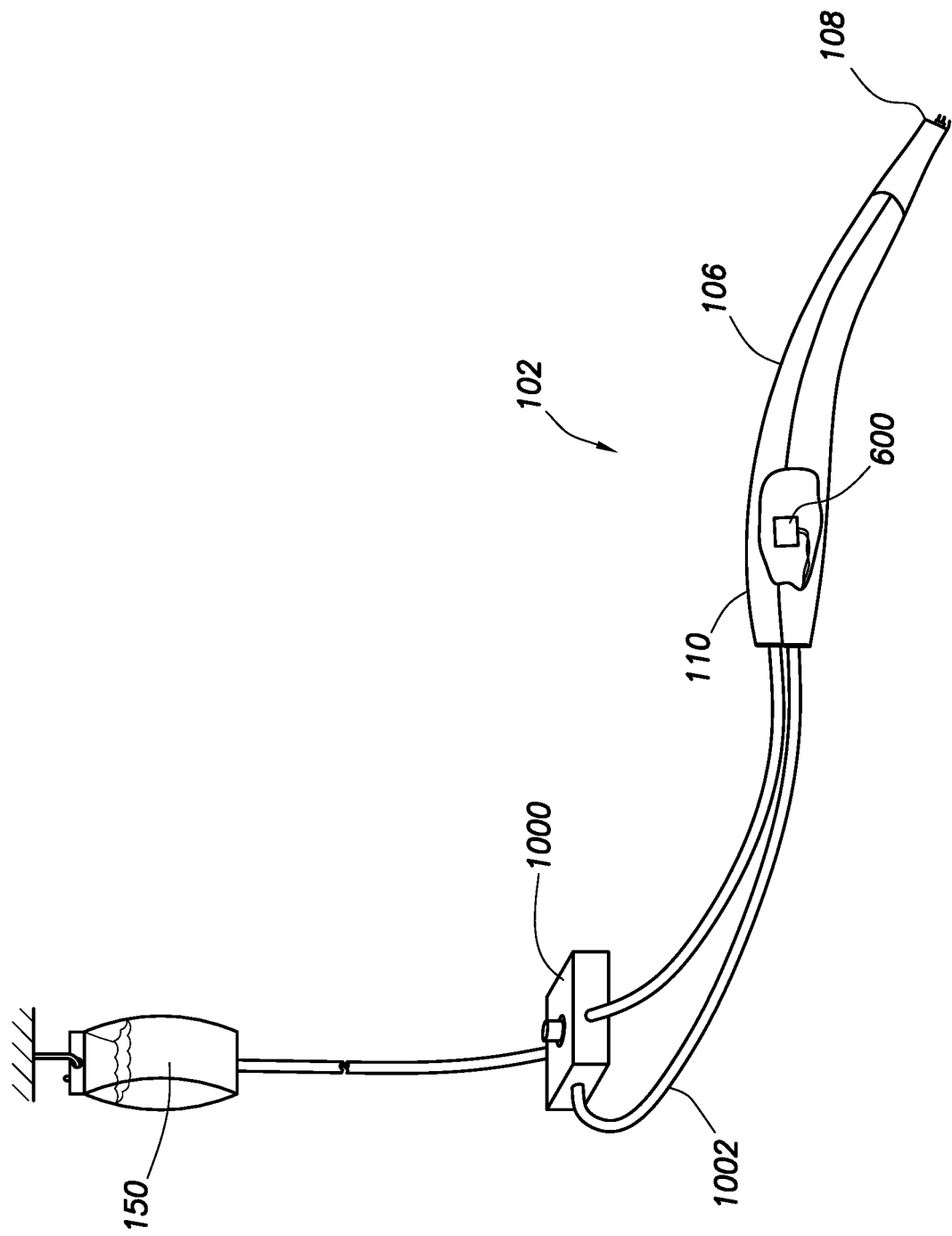
FIG. 10 shows an elevation view of a (partial) system in accordance with at least some embodiments.

The example systems discussed to this point have assumed that the controller 104 is directly responsible for reading orientation information from the orientation sensor 600 and commanding the flow control device 152 to change the restriction to the flow of conductive fluid. However, in yet still other example embodiment the adjustments to conductive fluid flow may be controlled logically outside the controller 104. FIG. 10 shows an elevation view of a system in accordance with yet still further embodiments. In particular, in the example system of FIG. 10 the flow control device 1000 is a standalone device that is directly communicatively coupled to the orientation sensor 600 by way multi-conductor cable 1002. The electrical coupling of the wand 102 to the controller 104 would still be present, but is not shown in FIG. 10 so as not to unduly complicate the figure. Moreover, the wand 102 will likewise still couple to a source of vacuum, but again such is not shown so as not to unduly complicate the figure.

Operation of the example system of FIG. 10 is similar to the previous embodiments. When a change in orientation (e.g., inclination, elevation, rotational-orientation) of the wand 102 is sensed, the flow control device 1000 may change the restriction to flow of conductive fluid to keep the flow substantially the same in spite of the orientation change, or to implement a predetermined flow strategy based on the orientation. All the example methods discussed above (and below) are applicable to the example system of FIG. 10.

Figure 11:
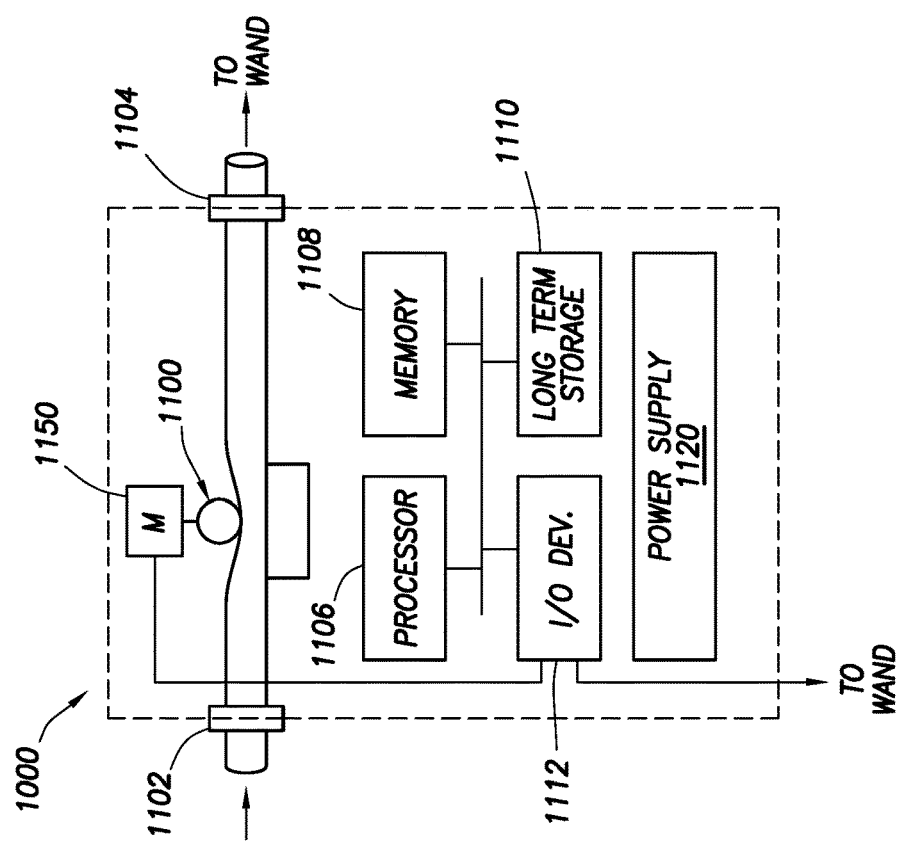
FIG. 11 shows an electrical block diagram of a flow control device in accordance with at least some embodiments.

FIG. 11 shows a schematic diagram of flow control device 1000 in accordance with example systems. In particular, flow control device 1000 comprises a valve 1100 of similar design, construction, and operation as discussed with respect to FIG. 8. For that reason, the operation of the valve 1100 will not be discussed again here in detail. While a "pinch" type valve is shown, a valve such as shown in FIG. 7 may be equivalently used. Similarly, flow control device 1000 comprises connectors 1102 and 1104 associated with the tubing, where the connectors are similar to those discussed in FIGS. 7 and 8, and so will not be discussed again here. However, the flow control device 1000 of FIG. 11 also comprises a computer system comprising a processor 1106 coupled to a memory 1108 (e.g., RAM memory) and also coupled to a long term storage device 1110 (e.g., ROM, battery backed RAM, flash memory). The long term storage device 1110 may store programs that are copied to the memory 1108 and executed by the processor 1106, including programs to implement the various embodiments disclosed herein. Also coupled to the processor 1106 in an input/output (I/O) device 1112, which I/O device 1112 enables the processor to be communicatively coupled to the valve operator of valve 1100, as well as to be communicatively coupled to the orientation sensor 600 in the wand 102. The precise nature of the I/O device 1112 depends on the communication system by which the valve operator and orientation sensor communicate (e.g., analog signals, parallel digital signals, serial digital communications). It is noted that the different I/O devices may be used as between the valve operator and the orientation sensor.

The example flow control device 1000 further comprises a power supply 1120 which may supply power to all the devices of the flow control device that need power. The electrical connections between the power supply 1120 and the remaining components of the flow control device 1000 are not shown so as not to unduly complicate the figure. In some example systems, the power supply 1120 is a battery or battery system. In other cases, the power supply 1120 takes power from a standard wall socket, and coverts the energy into a correct format for the various devices of the flow control device 1000 (e.g, converts 120 VAC from the wall socket to 3.3 VDC for the electronic components, and 12 VDC for valve operator 1150). In the example system standalone system, operational power for the orientation sensor 600 may be provided from the flow control device 1000.

Figure 12:
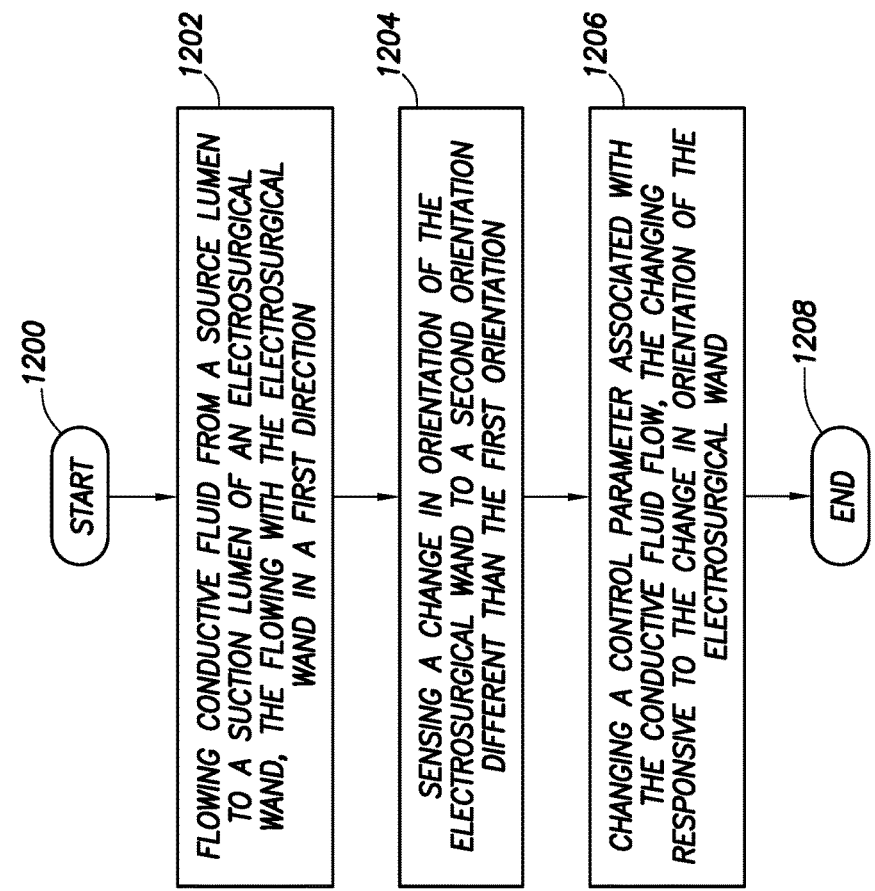
FIG. 12 shows a method in accordance with at least some embodiments.

FIG. 12 shows a method in accordance with at least some embodiments, portions of which may be implemented by software executing on a processor. In particular, the method starts (block 1200) and comprises: flowing conductive fluid from a source lumen to a suction lumen of an electrosurgical wand, the flowing with the electrosurgical wand in a first orientation (block 1202); sensing a change in orientation of the electrosurgical wand to a second orientation different than the first orientation (block 1204); and changing a control parameter associated with the conductive fluid flow, the changing responsive to the change in orientation of the electrosurgical wand (block 1206). Thereafter, the methods ends (block 1208), likely to be immediately repeated when orientation of the wand again changes.

From the description provided herein, those skilled in the art are readily able to combine software created as described with appropriate general-purpose or special-purpose computer hardware to create a computer system and/or computer sub-components in accordance with the various embodiments, to create a computer system and/or computer sub-components for carrying out the methods of the various embodiments and/or to create a non-transitory computer-readable medium (i.e., not a carrier wave) that stores a software program to implement the method aspects of the various embodiments.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. A system comprising:
    an electrosurgical controller, the electrosurgical controller configured to produce radio frequency (RF) energy at an active terminal with respect to a return terminal;
    an electrosurgical wand coupled to the electrosurgical controller, the electrosurgical wand having:
        an orientation sensor, readings from the orientation sensor indicative of orientation of a first portion of the wand relative to a second portion of the wand, different than the first portion;
        an active electrode defined on a distal end of the electrosurgical wand;
        a lumen in operational relationship to the active electrode, the lumen coupled to tubing, the tubing and lumen configured to flow an electrically conductive fluid therethrough; and
    a flow control device coupled to the tubing, the flow control device operatively coupled to the orientation sensor; wherein the system is configured to sense a change of orientation of the wand, and responsive to the change of orientation change a control parameter associated with the flow control device, wherein the flow control device adjusts a flow of fluid at a first flowrate through the lumen if the wand is orientated such that the lumen is disposed above the active electrode, and adjusts a flow of fluid at a second flowrate, different from the first flowrate, upon the wand being rotated such that the lumen is disposed below the active electrode.

2. The system of claim 1 wherein the orientation sensor is at least one selected from the group consisting of: an inclinometer; a gyroscope; a three-axis gyroscope; a six-axis gyroscope.

3. The system of claim 1 wherein the flow control device is a pump operatively coupled with the tubing.

4. The system of claim 1 further comprising:
    wherein the orientation sensor is communicatively coupled to the electrosurgical controller;
    wherein the flow control device is operatively coupled to the electrosurgical controller; and
    wherein the electrosurgical controller is configured to determine orientation of the electrosurgical wand and change a control parameter of the flow control device.

5. The system of claim 1 wherein the system is configured to sense a change of orientation of the wand, and responsive to the change of orientation change a control parameter of the flow control device so as to compensate for changes of quantity of electrically conductive fluid flow adjacent the active electrode as a result of changes of orientation.

6. The system of claim 1 wherein the system is configured to generate an ionized vapor adjacent the active electrode and wherein changing the control parameter of the system is configured to form a more uniform ionized vapor as the wand orientation changes.

7. The system of claim 1 wherein the orientation sensor senses rotational orientation of the wand.

8. The system of claim 1 wherein the system restricts the flow of fluid at a first limit if the wand is orientated such that the lumen is disposed above the active electrode and wherein the system restricts the flow of fluid at a second limit, different from the first limit, upon the wand being rotated such that the lumen is disposed below the active electrode.

9. The system of claim 1 wherein the system is configured to coagulate tissue adjacent the active electrode and wherein the change in control parameter of the flow control device is configured to maintain efficient coagulation as the wand orientation changes.

10. A system comprising:
    an electrosurgical controller, the electrosurgical controller configured to produce radio frequency (RF) energy at an active terminal with respect to return terminal;
    an electrosurgical wand coupled to the electrosurgical controller, the electrosurgical wand comprising:
    an orientation sensor, readings from the orientation sensor indicative of elevation of a first portion of the wand relative to a second portion of the wand, different than the first portion;
    an active electrode defined on a distal end of the electrosurgical wand;
    a lumen adjacent to the active electrode, the lumen coupled to tubing, wherein the tubing and lumen are configured to flow an electrically conductive fluid therethrough; and
    a flow control device coupled to the tubing, operatively coupled to the orientation sensor;
    wherein the system is configured to sense a change of elevation of the wand, and responsive to the change of elevation, change a control parameter of the flow control device; and wherein the system is configured to vaporize the electrically conductive fluid adjacent the active electrode sufficient to ablate tissue and wherein changing the control parameter is configured to maintain efficient vaporization as the wand elevation changes.

11. The system of claim 10 wherein the orientation sensor readings indicate a relative location of the lumen relative to the active electrode.

12. The system of claim 10 wherein the system is configured to change a control parameter associated with the flow control device responsive to the change of elevation, wherein the flow control device adjust a flow of fluid at a first flowrate through the lumen if the wand is orientated such that the lumen is disposed above the active electrode and adjusts a flow of fluid at a second flowrate, different from the first flowrate, such that the lumen is disposed below the active electrode.

13. The system of claim 10 wherein the orientation sensor is at least one selected from the group consisting of: an inclinometer; a gyroscope; a three-axis gyroscope; a six-axis gyroscope.

14. The system of claim 10 wherein the flow control device is a pump coupled within the tubing.

15. The system of claim 10 further comprising:
wherein the orientation sensor is communicatively coupled to the electrosurgical controller;
wherein the flow control device is operatively coupled to the electrosurgical controller; and
wherein the electrosurgical controller is configured to determine elevation of the electrosurgical wand and change the control parameter of the flow control device.

16. The system of claim 10 wherein the system is configured to change a control parameter of the flow control device to as to compensate for changes of fluid flow adjacent the active electrode as a result of changes in elevation.

17. The system of claim 10 wherein the orientation sensor is disposed within an interior volume of a handle of the wand.

18. The system of claim 10 wherein the system is configured to coagulate tissue adjacent the active electrode and wherein the change in control parameter of the flow control device is configured to maintain efficient coagulation as the wand elevation changes.

* * * * *